United States Patent
Elistratov

(10) Patent No.: US 10,064,421 B2
(45) Date of Patent: Sep. 4, 2018

(54) BIOLOGICALLY ACTIVE FOOD SUPPLEMENT

(71) Applicant: Dmitriy G. Elistratov, Penza (RU)

(72) Inventor: Dmitriy G. Elistratov, Penza (RU)

(73) Assignee: Parapharm LLC, Penza (RU)

( * ) Notice: Subject to any disclaimer, the term of this patent is extended or adjusted under 35 U.S.C. 154(b) by 0 days.

(21) Appl. No.: 15/062,161

(22) Filed: Mar. 6, 2016

(65) Prior Publication Data

US 2016/0192687 A1    Jul. 7, 2016

Related U.S. Application Data

(63) Continuation-in-part of application No. 14/138,875, filed on Dec. 23, 2013, now abandoned, which is a continuation-in-part of application No. 13/256,237, filed on Sep. 13, 2011, now abandoned.

(51) Int. Cl.

| | | |
|---|---|---|
| *A61K 36/00* | (2006.01) | |
| *A61K 35/64* | (2015.01) | |
| *A23L 1/302* | (2006.01) | |
| *A61K 31/355* | (2006.01) | |
| *A61K 31/375* | (2006.01) | |
| *A61K 31/575* | (2006.01) | |
| *A61K 36/28* | (2006.01) | |
| *A61K 47/02* | (2006.01) | |
| *A61K 47/12* | (2006.01) | |
| *A61K 47/26* | (2006.01) | |
| *A23P 10/28* | (2016.01) | |
| *A23L 33/10* | (2016.01) | |
| *A23L 33/105* | (2016.01) | |
| *A23L 33/15* | (2016.01) | |
| *A23L 33/16* | (2016.01) | |
| *A61K 35/63* | (2015.01) | |

(52) U.S. Cl.
CPC ............... *A23L 1/302* (2013.01); *A23L 33/10* (2016.08); *A23L 33/105* (2016.08); *A23L 33/15* (2016.08); *A23L 33/16* (2016.08); *A23P 10/28* (2016.08); *A61K 31/355* (2013.01); *A61K 31/375* (2013.01); *A61K 31/575* (2013.01); *A61K 35/63* (2015.01); *A61K 35/64* (2013.01); *A61K 36/28* (2013.01); *A61K 47/02* (2013.01); *A61K 47/12* (2013.01); *A61K 47/26* (2013.01); *A23V 2002/00* (2013.01)

(58) Field of Classification Search
CPC ................................ A61K 36/00; A61K 35/64
See application file for complete search history.

*Primary Examiner* — Rosanne Kosson
(74) *Attorney, Agent, or Firm* — Patentagar PLLC; Alexander Rabinovich

(57) ABSTRACT

A biologically active food additive comprises an ecdysteroid medicinal herb, such as *Rhaponticum carthamoides* (5-70 wt. %), drone brood (1-70 wt. %), ascorbic acid (3.6-70 wt. %), vitamin E (0.05-30 wt. %), and vehicles, such as calcium stearate, talc, lactose (the balance). The additive contributes to increasing the muscle weight in athletes, maintaining testosterone level, and demonstrates anabolic, anticatabolic and potency enhancing effects.

5 Claims, No Drawings

BIOLOGICALLY ACTIVE FOOD SUPPLEMENT

CROSS-REFERENCE TO RELATED APPLICATIONS

This application is a continuation in part of U.S. application Ser. No. 14/138,875 filed on Dec. 23, 2013, which is a continuation in part of U.S. application Ser. No. 13/256,237 filed on Sep. 13, 2011, which is a U.S. National Stage application of International application PCT/RU2010/000098 filed on Mar. 3, 2010, which claims priority of Russian Federation application RU 2009109273 filed on Mar. 13, 2009, all of the above applications being incorporated herein by reference in their entirety.

FIELD OF THE INVENTION

The invention relates to food industry, and specifically, to biologically active food additives, and is intended for increasing muscle weight in athletes and maintaining testosterone level, while providing anabolic, anticatabolic and potency enhancing effect.

BACKGROUND OF THE INVENTION

The best biostimulators and energetically rich products are the preparations developed from bee hive products. The preparation "Tonus" is known, which was developed from pollen and milk sugar (lactose). This preparation is produced by company "Biokor". However, this preparation does not contain a multivitamin complex or any vital microelements. Its effect on a human body is explained strictly by the presence of pollen, which could complicate the interpretation of biological activity of the "Tonus" as it becomes necessary to know precisely when the pollen was collected and from what plants. The closest prototypes to the invention in terms of the technical substance and achievable result are the natural multivitamin complex Leveton (RU 2,066,963 filed 1993 Oct. 20) and APILAR tablets (RU 2,233,666 filed 2002 Dec. 30) based on drone brood.

According to RU 2,066,963, Leveton contains pollen (pollen load), leuzea (*Rhaponticum carthamoides*), ascorbic acid, alpha-tocopherol acetate, propolis, calcium stearate, talc and lactose at the following ingredient ratio (wt. %): Pollen (pollen load): 50-51; *Rhaponticum carthamoides:* 10; Ascorbic acid: 3.0-3.5: Alpha-tocopherol acetate: 0.15; Propolis: 2; Calcium stearate: 0.92-0.95; Talc—3; Lactose—the balance.

Leveton effect is caused by a synergism of its ingredients: accurately dosed vitamins and phytoecdysteroid donors—*Rhaponticum carthamoides* and pollen (pollen load).

The objective of the development of Leveton was the creation of such a preparation, the main action mechanism of which would be influencing metabolism within cells. The preparation renders not only general strengthening and tonic effect on human body, but is also recommended for a preventive maintenance of the central nervous system dysfunction, treatment of prostate and erectile dysfunction."

According to RU 2,233,666. "APILAR"tablets have" . . . an anabolic and actoprotecting effect, the tablets containing adsorbed homogenate of drone brood (the homogenate, lactose, pectin, preservatives—sorbic and citric acids), as well as calcium stearate and flavorant as auxiliary substances at the following ingredient ratio in tablet mass per 100 tablets, g: Drone brood homogenate: 12.0-14.5; Lactose: 30.0-38.0; Pectin: 3.0-5.0; Sorbic acid: 0.1-0.4; Citric acid: 0.03-0.5; Sweetener: 0.05-0.5; Calcium stearate: 0.5-1.0; Flavorant: 0.1-0.5"

The prototypes have the following disadvantages: In the R. D. Seifulla's patent RU 2,066,963, the preparation targets the general strengthening and tonic effect on a human body. No information can be found in RU 2,066,963 with regard to the increase of muscle weight in athletes, maintenance of testosterone level, anabolic, anticatabolic or testosterone level effects. In addition, the preparation disclosed in RU 2,066,963 has substantial disadvantages, such as: (1) allergic effect of pollen; (2) rapid loss of the biological value of pollen during storage—a sharp decrease in activity versus time, as well as a destructive effect of temperature. Existing preservation technologies cannot guarantee complete preservation of pollen ingredients. A part of vitamins and amino acids is destroyed during the drying stage. Bees receiving pollen stored for a year in a refrigerator, have produced 56% less brood than those receiving fresh pollen. i.e. about half of the nutritious activity of flower pollen is lost. (3) Differences in chemical composition. Although Leveton is produced from pollen collected from miscellaneous herbs, the chemical composition of pollen varies from batch to batch, which makes the preparation unstable and should be taken into consideration by a coach when prescribing Leveton. (4) Intake method. The most effective method of pollen intake is sublingual, otherwise multiple useful substances contained in pollen are destroyed by digestive juices of the stomach. However, not all the people can tolerate such intake method.

Disadvantages of the APILAR tablets (RU 2,233,666 by D. S. Lazaryan) are the following: (1) Short shelf life and the need to be stored in a refrigerator. This can be explained as follows: Drone brood deteriorates very quickly. While royal jelly is acidic (pH=3.5-4.5) and, thus, possesses bactericidal properties, drone brood is neutral (pH=6.11±0.11), and, therefore, deteriorates quickly. It can be stored for no longer than 1 hour. Using after that can result in poisoning. (see Krivtsov N. I. et al., Theory and means of apitherapy. Publishing house OOO PKF "Komilfo", 2007). Therefore, APILAR tablets should be stored in a refrigerator and have a shelf life of 6 months. (0.2) It is noteworthy, that anabolic activity of APILAR tablets declared in RU 2,233,666 is not supported by its disclosure. Referring to Table 1 of this patent, the gain of weight in animals was as follows: when using placebo—15.91%; with Apilac—22.98%; and with APILAR tablets—only 13.53%, i.e. less than in case of placebo. For that very reason, APILAR tablets have not found the application in sports. Also, nowhere in RU 2,233,666 can a reference be found with regard to maintenance of testosterone level, anticatabolic and testosterone level effects.

Both prototypes have substantial disadvantages, which prevented their extended application in sports.

SUMMARY OF THE INVENTION

The present invention is free of the prototype disadvantages and also possesses the following pronounced effects: it increases the muscle weight in athletes, maintains testosterone level, and demonstrates anabolic, anticatabolic and potency enhancing effects. Up to date, no product was developed, which would render the same effect on a human body.

The effect of the proposed product does not represent a sum of effects of two previously known products. Unlike the closest prototypes of the proposed invention disclosed in RU 2,233,666 (APILAR tablets) and RU 2,066,963 (Leveton tablets), the technical result of the use of the proposed product is its ability to increase the muscle weight in athletes, maintain testosterone level, and demonstrate anabolic, anticatabolic and potency enhancing effects, which could not be achieved from the use of the substances disclosed in prior art.

It is noteworthy that RU 2,066,963 discusses the possibility of using larvae, this possibility having been rejected because "during the period of its development, the quantity of ecdysteroids may vary hundreds of times during a day, which could substantially affect the biological activity of the preparation. This does not allow having more precise dosage and, hence, more precise standardization." Besides, the simple joint use of the two prior art publications was not possible because *Rhaponticum carthamoides* is collected in the fall or in the early spring, when bees still (or already) do not fly, and hence, do not produce drone brood. For this reason, the applicant failed to find combining drone brood with not only *Rhaponticum carthamoides* but also with any other medicinal herb.

Therefore, the practical issue was to create a product, which would allow maintaining biological properties of the drone brood for a long time, and would be convenient to use.

According to the invention, a biologically active food additive, comprising *Rhaponticum carthamoides* (or a medicinal herb containing ecdysteroids), ascorbic acid (vitamin C), vitamin E, and vehicles (such as calcium stearate, talc, lactose), additionally comprises drone brood, the ingredient ratio (wt. %) being: Drone brood: 1-70; *Rhaponticum carthamoides* (or a medicinal herb containing ecdysteroids): 5-70; Ascorbic acid: 3.6-70; Vitamin E: 0.16-30; Vehicle—the rest (the balance).

DETAILED DESCRIPTION OF THE INVENTION

The explanation of the above composition is as follows:

Drone brood differs from the pollen in that it does not cause allergic reaction and is stable in terms of biological effect, as well as it contains a multiple functional groups of sulfide group enzymes and hormones-testosteroids, progesterone and estradiol. Due to such set of substances, drone brood promotes accelerated recovery of biochemical and mass metric characteristics of seminal and prostate glands by acting as a stimulant of the central mechanisms of androgen formation intensity regulation.

Biochemical composition of drone brood includes proteins—10-20% (including up to 11.4% of amino acids); carbohydrates: 1-5.5% (including up to 5% of glucose; up to 0.5% of fructose and up to 0.5% of sucrose); and fats: 5-6.3%.

Microelements (mg %) in drone brood: K—0.50; Na—38; Ca—14; P—189; Mg—2; Fe—3.23; Mn—4.40; Zn—5.54, Cu—2; Cr, Co, Ni, Ag, Au, etc.

Vitamins (water- and fat-soluble) in drone brood: A—0.54 I.U./g; xanthophyll—0.297 mg %; β-carotene—426 I.U./g; $B_2$—0.739 mg %; D—950 I.U./g; choline—442.8 mg %; nicotinic acid—15.8 mg %.

Drone brood increases metabolism level during active muscle activity, which results in enhanced physical endurance. Drone brood contains 10 times more steroid hormones, than pollen. Drone bee larvae used for preparing drone brood for the additive according to the present invention are extracted in accordance with a method disclosed in US patent application 2014/0323014 incorporated herein in its entirety as a reference. Drone brood used in the additive according to the present invention is prepared in accordance with a method disclosed in US patent application 2015/0030640 incorporated herein in its entirety as a reference.

The inclusion of increased doses of vitamins C and E helps enhancing the anticatabolic and antioxidant effects of the proposed invention.

It is stated in "Allowed medicinal products and BAA—a guidance for body builders and weightlifters" by T. V. Bubnova (in Rus.), Penza State Pedagogical University, Methodical recommendations, p. 14: "During intensive physical activities, an accelerated vitamin destruction and clearance from the body takes place, causing the need in them to increase. It is known, for example, that performance of moderate and heavy work . . . requires an increase in vitamin supply to the body by 1.5-3 times". The same publication references the daily vitamin need for a body of a person not engaged in physical activities (Table 3, p. 15) as: Vitamin C—50-100 mg, and for a person engaged in physical activities (Table 4, p. 16), as: Vitamin C—120-250 mg", i.e. the prior art composition fail to satisfy the body need in vitamin C. The suggested ratio in the proposed invention, on the other hand, provides the antioxidant protection of the body exposed to increased loads.

It should also be emphasized that the presence of increased doses of vitamin C in the proposed invention is a mandatory condition, since vitamin C enables control of fluctuations of cortisone level caused by weight training. Cortisone is a hormone that destroys muscles and is capable of turning metabolism in a catabolic direction. Increased level of cortisone destroys muscle tissue.

Joint application of vitamins C and E, along with drone brood and *Rhaponticum carthamoides*, enhances antioxidant and anticatabolic effect of these vitamins.

The proposed product can use various substances as a vehicle (filler). A non-limiting list of the substances comprises precipitated silica, precipitated sodium aluminosilicate, precipitated calcium silicate, Aerosil® (colloid silicic acid), colloidal silicon dioxide, abrasive silicon dioxide, sugar, milk sugar (lactose), anhydrous lactose, fructose, ribose, hydroxypropyl methylcellulose (thickener), hydroxypropyl methylcellulose—substitution type 2208 (hydrophilic matrix agent), hydroxypropyl methylcellulose acetate succinate—an agent for gastro-resistant coating, low-substituted hydroxypropyl methylcellulose, oxypropyl methylcellulose, cellufluor, acethylphtalylcellulose, microcrystalline cellulose, wheat flour, dibasic calcium phosphate, dextrose (glucose), converted starches, completely pregelatinized potato starch, native potato starch, native cornstarch, completely pregelatinized cornstarch, partially gelatinized cornstarch, partially hydrolyzed cornstarch, cross-carmellose sodium, heavy magnesium carbonate, magnesium stearate, vegetable magnesium stearate, calcium stearate, sodium starch glycolate, salts of iron, salts of potassium, salts of sodium, salts of calcium, salts of magnesium, salts of zinc, sodium stearyl fumarate, stearic acid, talc, titanium dioxide, Kollidon® (polyvinylpyrrolidone), Kollidon® CLM, Kollidon® CL, Kollidon® 25, Kollidon® 30, Kollidon® 90, Kollidon® SR, Polyplasdone® XL.

While searching the sources of scientific, technical and patent information, no substance was found that would possess a similar combination of essential features enabling the same positive effect. Thus, the proposed invention represents a technical solution to the problem, demonstrating novelty, inventive level and industrial applicability. A therapeutic and preventive product is produced in the form of tablets. The lower limit is determined by convenience of use of the proposed complex, i.e. the use of lower quantity of tablets. The upper limit is determined by the fact that at a higher percentage ratio, it will be difficult to obtain a tablet: it will break up.

Example 1 of the Complex Formulation for a 500 mg Tablet

Drone brood—10 mg;
*Rhaponticum carthamoides* (or a medicinal herb containing ecdysteroids)—50 mg;
Ascorbic acid—50 mg;
Vitamin E—5 mg;
Vehicles—385 mg.

It is important to emphasize the role of vehicles in the proposed product. Without vehicles it would be impossible to create the proposed product and, in particular, combine *Rhaponticum carthamoides* and drone brood. The specified ascorbic acid and vehicle content allowed achieving preserving effect, while retaining all properties of *Rhaponticum carthamoides* and drone brood.

Thus, the proposed biologically active additive created from *Rhaponticum carthamoides* (or a medicinal herb containing ecdysteroids), drone brood, ascorbic acid (vitamin C), vitamin E, and vehicles can be used as a means for building up muscle weight in athletes due to increased content of phytoecdysteroids, which are phytohormones affecting anabolic processes in the athlete's body. However, the preparation renders not only anabolic effect on a human body, but is also recommended for prevention of the central nervous system dysfunction, as well as treatment of prostate disease and erectile dysfunction.

Also, the use of the proposed product reliably promotes anticatabolic processes in the muscle tissue for types of sports characterized by developing building endurance. S. N. Portugalov has studied the effect of the proposed product on Mordovian race walkers during a training camp in Adler. The walkers specialize in race walking the distance of 20 and 50 km. This category of athletes does not require the growth of muscle weight. It was found that the effect of the proposed product on the body composition parameters during body fat assessment test was as follows.

|  | Before use | | After use | |
| --- | --- | --- | --- | --- |
| Parameters | Test | Check | Test | Check |
| Body weight, kg | 65.8 ± 0.4 | 66.1 ± 0.25 | 64.6 ± 0.2 | 64.8 ± 0.4 |
| Muscle wetght, kg | 34.15 ± 0.16 | 34.23 ± 0.12 | 33.99 ± 0.10* | 32.48 ± 0.20 |
| % | 51.9 ± 0.1 | 51.8 ± 0.1 | 51.7 ± 0.2* | 50.9 ± 0.4 |
| Fat weight, kg | 5.85 ± 0.12 | 5.9 ± 0.2 | 5.29 ± 0.24 | 5.57 ± 0.20 |
| % | 8.9 ± 0.1 | 9.4 ± 0.12 | 8.29 ± 0.2 | 8.6 ± 0.16 |

*Deviations between the test and control were statistically insignificant.

Shown below is a variation of the overall testosterone blood level in the athletes before and after the experimental educational and training camp.

| Group | Initial level | Final level |
| --- | --- | --- |
| Control | M 22.4 ± 0.8 | M 18.6 ± 1.0 (p < 0.05) |
|  | F 3.6 | F 2.1 |
| Test | M 20.9 ± 0.4 | M 19.8 ± 0.8 (p > 0.05) |
|  | F 2.4 | F 2.5 |

In the course of the study: "Effect of the "proposed product" on athlete body load adaptation characteristics," the level of adaptation in track-and-field athletes/runners with respect to endurance was assessed from dynamics of biochemical control characteristics of blood during training. Within the scope of this study, the control of biochemical characteristics was based on athlete blood samples drawn in the morning on an empty stomach after one day of resting. In the blood samples, the quantitative content of hemoglobin (HB), urea, lactate, glucose, magnesium (Mg), phosphorus (P), testosterone was determined:

It was determined as a result of conducted measurements that no reliable differences existed between the athletes of the test group and control group with respect to the dynamics of the levels of HB, urea, lactate, glucose. Mg, and P: the testosterone level in athletes of the control group decreased by the average of 16.9% (p<0.05) by the end of the education and training camp; whereas, unlike the control group, no reliable variation of testosterone level was detected in athletes of the test group during the same time period.

It is important to note that testosterone level studies or the effect of Leveton or Apilar on human testosterone level were mentioned in neither of the RU 2,233.666 or RU 2,066,963.

It is believed that for the first time, the applicant managed to create a product rendering strong effect on human testosterone level without the use of the doping means, and ensure the anabolic, anticatabolic and potency enhancing effects.

With anticatabolic effect in view in particular, it is well known that one of the factors restricting physical performance of highly trained athletes and limiting their score level is a conflict between the demands of intensifying the training load and ultimate activation of body's catabolic processes observed thereat. A research relating to anticatabolic action of four non-doping preparations was conducted with regard to their effect on the level of urea in blood serum in the course of exhaustive muscle loading. The increase of the urea concentration in blood attests to enhancing catabolic processes in the sportsman's body. Accordingly, the degree of the increase reflects the anticatabolic effect of the preparations administered. 20 male weightlifters at the ages from 16 to 23 in the weight category of up to 94 kg were divided by random sampling technique into four groups to take the following preparations: tablets of drone brood with 60 mg of active substance ($1^{st}$ group): Leveton tablets of 500 mg for the $2^{nd}$ group, each tablet comprising pollen (50-51%). *Rhaponticum cardamoides* (10%), vitamin C (ascorbic acid)—3.0-3.5%, vitamin E—0.15%, propolis (2%), calcium stearate (0.92-0.95%), talc (3%), lactose (the balance); 500 mg tablets of Leveton Forte (the proposed product) for the $3^{rd}$ group, each tablet comprising root of *Rhaponticum cartamoides*—70 mg, drone brood—100 mg, vitamin C—50 mg, vitamin E—10 mg, vehicles—the balance; the $4^{th}$ group was administered 500 mg tablets of a combination product, each tablet comprising pollen—250 mg, drone brood homogenate—60 mg, *Rhaponticum car-*

*damoides*—50 mg, vitamin C—15 mg, vitamin E—0.75 mg, propolis—10 mg, calcium stearate—0.475 mg, talc—15 mg, lactose—the balance.

Throughout the research, the four groups, five athletes in each of them, were at a training camp with a high volume of daily intensive training loads at an anaerobic zone of energy supply aimed at strength and power training. Initially, the athletes in the groups did not differ from each other, as far as anthropometric data and the level of physical efficiency are concerned. In the course of the research, no negative impact of the administered preparations on the vital status of the athletes was observed in all the groups. The preparations contain no components having doping activity.

The athletes from the four group were taking three tablets of the respective preparations sublingually twice a day for 21 days, the last intake being no later than 6 p.m. Before the research and after its completion, serum urea value (in mg %) was determined in all the athletes with the following results.

| Group of athletes | Initial urea value | Urea value after 21 days of training and taking the preparations |
| --- | --- | --- |
| 1 | 26.0 ± 2.3 | 35.7 ± 2.1 |
| 2 | 25.9 ± 2.5 | 36.1 ± 2.2 |
| 3 | 26.2 ± 2.0 | 28.4 ± 2.0 |
| 4 | 26.1 ± 2.1 | 33.1 ± 2.1 |

The above results show that the serum urea values fall within the limits of the physiological norm (15-50 mg %) in all the athletes. However, the lowest result upon completing the research was observed in Group 3, which attests that the proposed product possesses the best anticatabolic effect. It is believed that anticatabolics target the level of cortisone, a hormone that is destructive of a muscle tissue and capable of channeling metabolism to catabolism. Hypercortisolism destroys muscle tissue. The proposed composition exerts a significant impact on the level of cortisone preventing it from rising, which usually occurs in the process of training. It is believed that this result stems from the joint use of *Rhaponticum carthamoides*, drone brood and vitamins C and E in the composition.

The applicant has also conducted studies to establish the effect of the proposed product on testosterone level. The following compositions were selected for the study:

Active ingredient content in the "Proposed Product 1":

| Ingredients | mg |
| --- | --- |
| Rhaponticum carthamoides | 100 |
| Drone brood | 100 |
| Vitamin C | 30 |
| Vitamin E | 3 |

Active ingredient content in the "Proposed Product 2":

| Ingredients | mg |
| --- | --- |
| Rhaponticum carthamoides | 50 |
| Drone brood | 50 |
| Vitamin C | 30 |
| Vitamin E | 3 |

The clinical study was conducted in 30 males with erectile dysfunction. The inclusion criteria were age-related:

Age 19-60 (sampling restriction based on age is associated with frequent detection in males older than 60 of the pronounced organic brain and somatic pathology, as well as paracmastic processes);

Consistence of the patient condition at the time of inclusion with the ICD-10 diagnostic criteria for F52.2

Failure of genital response, accompanied by one of following neurotic disorders: phobic anxiety disorders (F40); mixed manic depressive disorder (F41.2) and adjustment disorder (F43.2);

Absence of leading organic pathology in sexual disorder pathogenesis.

The study did not include patients with: alcoholism, drug addiction, anatomic penis deformations, confirmed endocrine ED causes, decompensated somatic diseases, the use of other means of ED treatment and preparations capable of causing ED.

All the patients have signed an informed consent form to participate in the study.

To implement the study objectives, the patients were separated into 3 therapeutic groups based on a simple randomization method—two test groups and one control group:

Group 1. Test group—12 patients with erectile dysfunction and combined psycho-emotional disorders, receiving "Proposed product 1" along with conventional psycho-pharmacotherapy.

Group 2. Test group—13 patients with erectile dysfunction and combined psycho-emotional disorders, receiving "Proposed product 2" along with conventional psycho-pharmacotherapy.

Group 3. Control group consists of 5 patients with erectile dysfunction and combined psycho-emotional disorders, receiving conventional psycho-pharmacotherapy.

For the duration of 4 weeks the preparation "Proposed product 1" and "Proposed product 2" were prescribed in a dose of 2 tablets twice a day. 30 minutes before meals. The assessment of therapy results was conducted on day 28 of the treatment. Restoration of sexual life was considered as the main criterion of the treatment efficacy.

As early as by day 7 since the start of therapy using preparations "Proposed product 1" and "Proposed product 2" in both test groups, the patients have noted subjective mood improvement, increase in self-validation and confidence in their sexual potential, decrease of strain and reduction of conflicts in their marital relations, as well as increase in frequency of spontaneous erections.

The study of the efficacy of the "Proposed product 1" and "Proposed product 2" relative to the sexual function of patients considering the clinical and dynamic variation of testosterone blood level has shown the following results:

Testosterone Level Dynamics Since the Beginning of Therapy

|  | Average cumulative characteristics | | | | | |
|---|---|---|---|---|---|---|
|  | Group 1 (n = 12) | | Group 2 (n = 13) | | Group 3 (n = 5) | |
| Studied parameter | Before treatment | After 28 days | Before treatment | After 28 days | Before treatment | After 28 days |
| Total testosterone | 11.8 ± 4.4 | 14.6 ± 5.2 | 14.5 ± 4.7 | 17.3 ± 5.6 | 12.9 ± 4.7 | 13.1 ± 5.8 |

In Group 1, where the preparation "Proposed product 1" was used, the testosterone level increased by 23.7%, and in Group 2, where the preparation "Proposed product 2" was used, the testosterone level increased by 19.8%.

By day 28, an increase in sexual function parameters, such as sex drive and erection, during therapy using "Proposed product 1" and "Proposed product 2" was established in 66.7 and 61.5% of the patients, respectively. The average sex drive increase was 28.0 and 24.3%, and erection increase −21.4 and 17.8%, respectively. In the Control group the fluctuations of testosterone level were insignificant.

It is necessary to note another important fact of using the proposed product—it is doping free. The extended use of the proposed product does not suppress production of its own hormones by the human body. It has been established that upon the extended use of the proposed product, testosterone levels in human body reach reference values, at which point any further growth stops. Continuing use of the proposed product does not result in either increase or decrease in testosterone level.

Anticatabolic action of the proposed product has found widespread use among athletes—body builders, who actively use testosterone drugs (forbidden in official sports). These athletes develop a so-called "throwback" problem. After proceeding with the treatment by "chemistry", and specifically, using exogenous testosterone drugs, an atrophy of male endocrine organs occurs. Therefore, there is an urgency in being able to rapidly restore such organs upon termination of steroid drug use, since at this time the body builder's body experiences low level of endogenous testosterone. As a result, catabolic processes start prevailing within the body leading to substantial drop in the muscle weight built up while using "chemistry".

The use of the proposed product considerably accelerates the restoration of endogenous testosterone in athletes—body builders, which allows achieving more powerful results in preservation of the muscle weight after a course of "chemistry" compared to no-use of the proposed product.

It is necessary to note that none of the prior art had such an application.

Conducted preliminary observations among athletes (masters of sports, masters of sports of international level) taking the proposed product have shown its high efficacy relative to muscle weight build-up in comparison with Leveton (102%). *Rhaponticum carthamoides* (106%) and APILAR (drone brood (103%)), which is a very good result for highly qualified athletes. According to the order of the Russian Ministry of Sports and Tourism regarding "weight-lifting", the following qualification norms were established for the "Masters of sports" title: for the 77 kg weight category, the norm is 280 kg: for the 83 kg weight category—295 kg: for the 94 kg weight category—310 kg. In other words, the difference is only 5% (295/280 and 310/295). Therefore, increase in performance by even 2% when using the proposed product is believed to be unexpectedly considerable.

| Groups of athletes | Avg body weight, kg | Avg muscle weight, kg | Avg fat weight, kg |
|---|---|---|---|
| 1. Initially | 92.30 | 58.4 | 9.2 |
| 1. After taking APILAR (drone brood) | 92.66 | 59.00 | 8.6 |
| 2. Initially | 91.70 | 59.51 | 7.33 |
| 2. After taking Rhaponticum carthamoides | 90.29 | 59.0 | 6.43 |
| 3. Initially | 90.1 | 57.75 | 8.11 |
| 3. After taking Leveton | 89.45 | 58.10 | 7.11 |
| 4. Initially | 85.3 | 56.06 | 6.9 |
| 4. After taking the proposed product | 86.7 | 58.36 | 6.0 |

It is necessary to emphasize that the effect of the proposed product is secured by the entire combination of all the ingredients of the proposed product, which individually do not possess this effect.

As a result, the proposed product has the following advantages compared to the prior art: it has lower sensitivity to storage conditions; it can be conveniently swallowed or dissolved by sucking; it does not comprise pollen, to which those taking the product may have allergy or intolerance; and it has marked anticatabolic effect and is able to maintain and/or restore the testosterone level.

It is worth mentioning that there is a difference in general between anabolic effect and the rise of the testosterone level. An example illustrating this distinction was described in the above by the case of patients with ED. The use of the proposed product resulted in increasing the level of testosterone, while anabolic effect was not observed. On the other hand, it is known (V. A. Margazin et al. "Clinical aspects of sport medicine." S.-Petersburg, SpetsLIT, 2013) that in sumo wrestlers, using *ginseng*, anabolic effect is pronounced while the testosterone level decreases. In experiment, after the treatment regimen with the use of the proposed product, the rise of the testosterone level was observed. This effect was not shown in neither of the compositions disclosed in RU2,066,963 and RU2,233,666.

What is claimed is:

1. A biologically active food additive comprising the following ingredients:
   a) an ecdysteroid-comprising medicinal herb;
   b) drone brood;
   c) ascorbic acid;
   d) vitamin E; and
   e) a vehicle; the additive ingredients being in the following ratio (wt. %): the drone brood: 1-70;

the ecdysteroid—comprising medicinal herb: 5-70; the ascorbic acid: 3,670; the vitamin E: 0.05-30; the vehicle—the balance, wherein the food additive does not comprise pollen, and whereby increasing the muscle weight in athletes, maintaining testosterone level, and anabolic, anticatabolic and potency enhancing effects are achieved when a therapeutically effective amount of the biologically active food additive is consumed.

2. The biologically active food additive according to claim 1, wherein the ecdysteroid-comprising medicinal herb includes *Rhaponticum carthamoides*.

3. The biologically active food additive according to claim 1, wherein the vehicle includes calcium stearate.

4. The biologically active food additive according to claim 1, wherein the vehicle includes talc.

5. The biologically active food additive according to claim 1, wherein the vehicle includes lactose.

\* \* \* \* \*

UNITED STATES PATENT AND TRADEMARK OFFICE
CERTIFICATE OF CORRECTION

PATENT NO. : 10,064,421 B2
APPLICATION NO. : 15/062161
DATED : September 4, 2018
INVENTOR(S) : Dmitriy G. Elistratov Page 1 of 1

It is certified that error appears in the above-identified patent and that said Letters Patent is hereby corrected as shown below:

On the Title Page

Replace (63) with the following:
Continuation-in-part of application No. 14/138,875, filed on Dec. 23, 2013, now abandoned, which is a continuation-in-part of application 13/256,237, filed on Sep. 13, 2011, now abandoned, which is a §371 application of PCT/RU2010/000098 filed on March 3, 2010, now abandoned.

Add item (30) as follows:
(30) Foreign Application Priority Data
March 13, 2009 (RU) ...................... 2009109273

In the Claims

Column 11, Line 2, Claim 1:
Replace the incorrect "...the ascorbic acid: 3,670..." with the correct "...the ascorbic acid: 3.6-70..."

Signed and Sealed this
Sixth Day of November, 2018

Andrei Iancu
*Director of the United States Patent and Trademark Office*